United States Patent [19]
Makoui

[11] Patent Number: 5,378,528
[45] Date of Patent: Jan. 3, 1995

[54] ABSORBENT STRUCTURE CONTAINING SUPERABSORBENT PARTICLES AND HAVING A LATEX BINDER COATING ON AT LEAST ONE SURFACE OF THE ABSORBENT STRUCTURE

[76] Inventor: Kambiz B. Makoui, 333 Winnebago Ave., Menasha, Wis. 54952

[21] Appl. No.: 776,557

[22] Filed: Oct. 15, 1991

Related U.S. Application Data

[62] Division of Ser. No. 511,452, Apr. 20, 1990, Pat. No. 5,128,082.

[51] Int. Cl.⁶ ............... A61F 13/15; A61F 13/20
[52] U.S. Cl. ................... 428/219; 428/237; 428/240; 428/283; 428/288; 428/290; 428/906; 604/365; 604/367; 604/368; 604/374
[58] Field of Search ............... 604/365, 368, 378, 367, 604/374; 428/290, 283, 219, 237, 240, 288, 906; 264/518; 156/276

[56] References Cited

U.S. PATENT DOCUMENTS

| | | | |
|---|---|---|---|
| 2,905,568 | 9/1959 | Burgeni | 117/11 |
| 2,955,641 | 10/1960 | Burgeni | 154/33 |
| 3,017,304 | 1/1962 | Burgeni | 154/54 |
| 3,575,749 | 4/1971 | Kroyer | 156/276 |
| 4,102,340 | 7/1978 | Mesek et al. | 604/365 |
| 4,103,062 | 7/1978 | Aberson et al. | 428/283 |
| 4,347,092 | 8/1982 | Hlaban et al. | 604/365 |
| 4,500,315 | 2/1985 | Pieniak et al. | 604/379 |
| 4,604,313 | 8/1986 | McFarland et al. | 428/283 |
| 4,640,810 | 2/1987 | Laursen et al. | 264/518 |
| 4,685,914 | 8/1987 | Holtman | 604/368 |
| 4,718,899 | 1/1988 | Itoh et al. | 604/368 |
| 4,721,647 | 1/1988 | Nakamishi et al. | 428/283 |
| 4,822,668 | 4/1989 | Tanaka et al. | 428/283 |
| 4,857,065 | 8/1989 | Seal | 428/283 |
| 4,902,559 | 2/1990 | Eschway et al. | 428/224 |
| 5,098,775 | 3/1992 | Harada et al. | 604/365 |

*Primary Examiner*—James D. Withers
*Attorney, Agent, or Firm*—R. Jonathan Peters

[57] ABSTRACT

A liquid absorbent structure is made by dry laying a fibrous web having incorporated therein a superabsorbent material, and applying a latex coating to at least one surface of the web, which on curing imparts integrity to the resulting structure without substantially impairing the effectiveness of the superabsorbent material to absorb liquid.

18 Claims, 4 Drawing Sheets

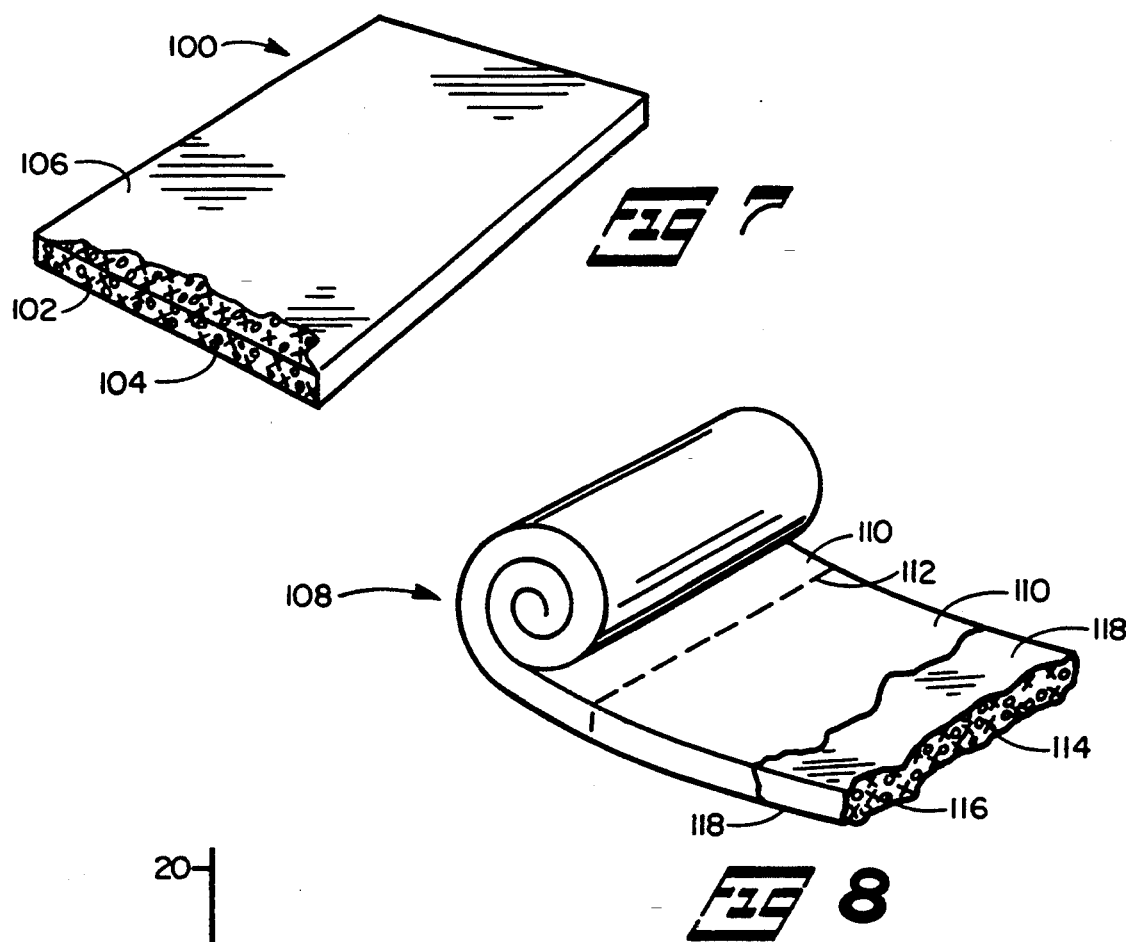
FIG 7
FIG 8
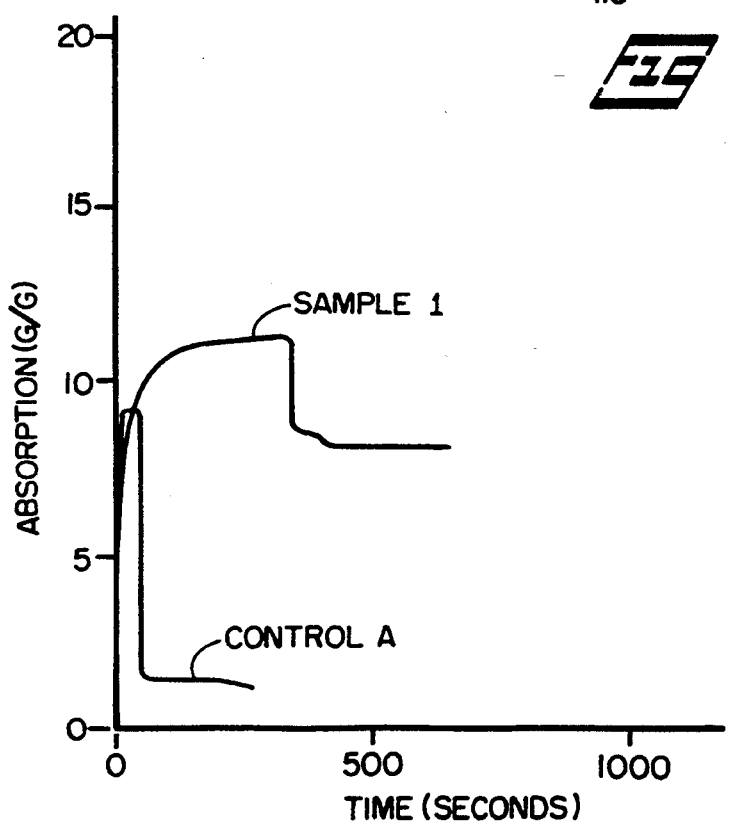
FIG 9

ABSORBENT STRUCTURE CONTAINING SUPERABSORBENT PARTICLES AND HAVING A LATEX BINDER COATING ON AT LEAST ONE SURFACE OF THE ABSORBENT STRUCTURE

This is a divisional of copending application Ser. No. 07/511,452 filed on Apr. 20, 1990, now U.S. Pat. No. 5,128,082.

FIELD OF THE INVENTION

This invention relates to liquid absorbent structures. In its more specific aspect, this invention relates to dry laid webs containing superabsorbent materials and stabilized with binder for use as liquid absorbent structures. Another aspect of the invention includes the method for making such structures.

BACKGROUND OF THE INVENTION AND PRIOR ART

Dry forming systems, and in particular air laying systems, in which the fiber orientation is randomly distributed in the plane of the web or fabric, are used now commercially in the manufacture of a variety of liquid absorbent products. Generally, in the air forming process the fibers, which may be cellulosic, synthetic, or a combination of both, are suspended in a gas stream (e.g., air) and then conveyed to a forming screen where the fibers are formed or condensed into a web. However, the resulting web lacks integrity, and therefore one of several techniques is used to bond the fibers and thereby stabilize the structure. The fabric products produced are soft, flexible and porous, and are suitable for a number of commercial products, particularly disposable products. The fiber content, at least to a large extent, used in many of these products is hydrophilic or can be rendered hydrophilic, and therefore the products are especially useful as liquid absorbent products, such as disposable diapers, incontinent pads, wipes, feminine napkins, and filtration materials.

In the conventional manufacture of air laid products, the loose web condensed on the forming screen is typically stabilized by mechanical, thermal, or chemical means. Mechanical or thermal means have been used extensively, and usually require fiber entanglement or fiber bonding. Chemical bonding utilizes a solvent or adhesive, and U.S. Pat. 3,575,749 to Kroyer discloses bonding the fibrous layer with a latex binder, which may be applied to one or both sides of the web. It has long been recognized, however, that chemical bonding with a latex binder is disadvantageous for use in certain products in that the binder impairs the wipe dry characteristic of the web in that the web has poor retention of the liquid.

More recently, water insoluble hydrogels or superabsorbent materials, typically in particle form, have been incorporated into the fibrous web in order to increase the absorptive capacity of the web. These hydrogels have an absorptive capacity for water and body fluids far exceeding that of the hydrophilic fiber, e.g. wood pulp fiber used in the web, and in fact are capable of absorbing twenty times or more their own weight of water and retain this fluid under pressure. Hydrogel particles have two serious limitations, however, that initially have militated against their acceptance in absorptive fibrous products. One limitation is the hydrogel particles, if not used properly, exhibit gel blocking, a phenomenon that inhibits liquid transmission to the interior; and, secondly, when hydrogel particles are incorporated into a web or fabric, the particles tend to migrate or sift and as a consequence, during manufacture, storage or use, the particles migrate from the useful part of the product or can be lost or cause dust. These limitations needed first to be resolved before hydrogels could be utilized to any appreciable extent in liquid absorbent products, e.g. disposable diapers. The prior art is replete with different mechanical means to achieve this objective, typically involving a roller compression or densification step. In U.S. Pat. No. 4,610,678 to Weisman et al., the web bearing the superabsorbent is densified by calender rolls, and the patent expressly avoids the use of solvents or other liquids which, as stated at column 2 of the patent, can impair the absorptive capability of the hydrogel and impart stiffness to the product. In U.S. Pat. No. 4,260,443 to Lindsay et al., the web containing hydrogel particles is embossed to provide land areas of adhesion and thereby confine the hydrogel to the desired areas. A disposable absorbent is disclosed in U.S. Pat. No. 4,500,315 to Pieniak et al., comprising a fibrous layered structure with the superabsorbent sandwiched between layers, and the composite is then compressed.

Still further, U.S. Pat. No. 4,640,810 to Laursen et al. discloses a system for forming an airlaid web, and proposes that a superabsorbent material may be incorporated into the web. The airlaid product is useful for disposable diapers, feminine napkins, underpads, and liquid filters. The patent also discloses in a general manner that the fibrous layer can be bonded to impart integrity to the web, and although alternate bonding methods are suggested, the patent describes using only heated embossing rollers in conjunction with the inventive process and apparatus. The background section of the Laursen et al. patent discusses the Kroyer patent, supra, but hastens to conclude that stabilizing the web or fabric with latex for absorbent products has numerous manufacturing disadvantages and drawbacks, and places complete emphasis on stabilizing the web with heated rolls and embossing.

In fact, the use of superabsorbent materials and latex in the same web or batt is considered counterproductive in that the latex, which in conventional practice is applied as an aqueous emulsion or dispersion or solution, will block the powder and impair or completely destroy its effectiveness. For example, U.S. Pat. No. 4,551,191 to Kock et al., which discloses an airlaid web containing superabsorbent material, states expressly that the absorption rate and capacity of the superabsorbent particles are adversely affected by certain process conditions such as those involving adhesives. This disadvantage was shown to be overcome by the teachings in U.S. Pat. No. 4,600,462 to Watt, which discloses that impairment of the water absorbency of the fiber caused by the latex binder can be overcome by substantially coating the fibers of the formed web with an aqueous solution of a water soluble hydrophile, preferably after the application of the binder. According to the Watt, the hydrophile interacts with the binding agent within the matrix to overcome water repellency.

This invention has therefore as its purpose to overcome the deficiencies of the prior art, and to provide a soft, absorbent structure that exhibits high integrity and relatively low bulk.

SUMMARY OF THE INVENTION

In its broadest aspect, the invention provides for a method of making a dry laid liquid absorbent structure that has high absorptive capacity, retention, and rate of absorption, and has stability or integrity, has a high basis weight, and has low bulk. According to the process of the invention, a dry laid web, preferably airlaid, is first formed having incorporated therein a water insoluble hydrogel or superabsorbent. A liquid latex is applied to at least one surface of the resulting web, and the latex is rendered active as by curing with heat. The latex is applied in sufficient quantity to impart integrity to the structure without substantially impairing the effective absorbent capacity of the hydrogel to absorb liquid by controlling the depth of penetration of the latex into the web and the degree of coverage of the hydrogel particles by the latex.

A conventional air forming system includes two or more distributors, and fibers are conveyed from each distributor to the forming screen, whereby plies of fibers are condensed on the screen as a web. The hydrogel or superabsorbent material may be incorporated into the fibrous plies or web at any convenient or desired point in the system, such as between plies or within the plies. Water insoluble hydrogels or superabsorbent materials, which are well known and commercially available polymeric materials, are applied to the fibrous layer or batt as a solid and in particulate form, which may include, for example, powders, particles, flake, fibers, globules, and the like. Typically, the hydrogel is distributed or deposited onto a layer or ply of fiber about midway during the formation of the web. Where desired, the absorbent structure may include a porous reinforcing web either as an outside layer, or as an interjacent layer with the hydrogel applied to one side only of the reinforcing web. A suitable reinforcing web may include, for example, creped paper, 3-D formed paper which is characterized by relatively large number of fiber-filled nubs, or scrim which typically is of a polyester or polyolefin material. The fibers used in the manufacture of the structure may be cellulosic or modified cellulosic, synthetic, or a combination, and may be either hydrophilic or hydrophobic. Such fibers include, for example, wood pulp fibers, rayon, polyethylene and polypropylene. When such fibers are dry laid, there is some mechanical entanglement but not sufficient to provide good integrity to the structure. A latex emulsion or solution, typically in an aqueous medium, is applied to one or both surfaces of the web to provide a latex coating which partially impregnates the web, and upon curing stabilizes the structure. The latex may be applied to the web by any suitable means such as spraying, brushing, flooding, rolling, and the like. The amount of latex applied and the degree of penetration of the latex are controlled so as to avoid impairing the effective absorbency of the hydrogel, thereby achieving a product of relatively high basis weight exhibiting on an area basis high absorbency as compared to similar prior art webs comprised of fiber and hydrogel only. This invention provides a web or pad that is thinner for equal area relative to the prior art webs, yet exhibits favorable absorbency and retention properties at a relatively high breaking length.

Because the fibrous structure of the present invention exhibits high liquid absorbency and retention, including body fluids, is soft, and has low bulk, the structure is especially useful in disposable products such as diapers, feminine pads, wipes, towels, and in filtration media.

BRIEF DESCRIPTION OF THE DRAWINGS

FIG. 7 is a perspective view of a wipe or towel embodying the structure of this invention, and partially broken away to illustrate the structure.

FIG. 8 is a perspective view of a partially rolled blank fabric structure and partially broken away to illustrate the details of the absorbent structure of the invention.

FIGS. 9 and 10 are graphs showing absorption and retention curves for an absorbent structure made in accordance with the invention with a one percent saline solution and with de-ionized water.

DETAILED DESCRIPTION OF THE INVENTION

The absorbent structures of the present invention may be made using conventional equipment designed for dry laying systems, and although the invention is described hereinbelow with particular reference to airlaid structures, it should be understood that other dry laid systems, e.g. carding, are also applicable.

Figure 1:
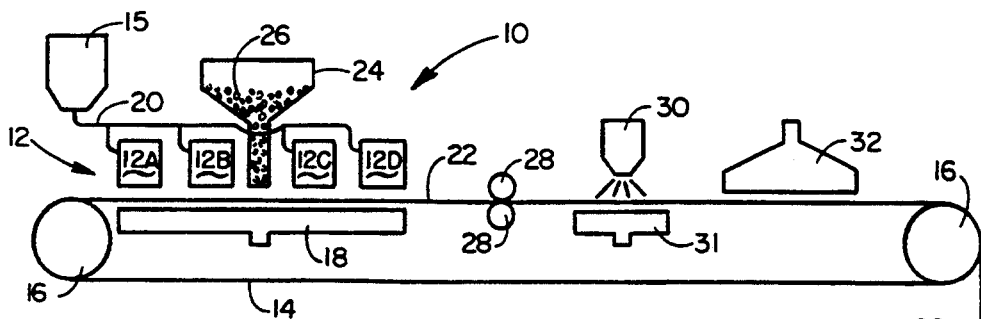
FIG. 1 is a schematic flow diagram of a process for making a liquid absorbent structure in accordance with the present invention.

Referring to the drawings wherein like reference numerals refer to similar parts throughout, there is shown in FIG. 1 a preferred embodiment for the manufacture of the liquid absorbent structure of the invention. In accordance with this embodiment, the air forming system, indicated generally by the numeral 10, includes a distributor unit 12 disposed transversely above a continuous forming screen 14 mounted on rollers 16 and driven by a suitable motor (not shown), and vacuum means or suction box 18 is positioned beneath the screen. In a conventional air forming system, upstream of the distributor unit is a defibrator or feeder (not shown), such as a hammermill or Rando-Feeder, where bales, laps or the like are defiberized, and further the fibers may be cleaned and/or blended if necessary or desired depending largely on the type of fibers used, the blend of fibers used, and the end product sought. For example, wood pulp fibers can be blended with synthetic fibers and applied as a blend by the distributor, or each distributor can convey a different fiber to the screen to form separate plies or layers. The fibers are carried by an air stream via conduit 20 to the distributors. The porous forming screen 14 is essentially coextensive with the distributors, and the suction box 18 beneath the screen draws the air stream downwardly and conveys the fibers to the surface of the screen thereby forming plies or a loose web 22. At this stage in the process, the web exhibits little integrity, and the vacuum means retains the loose, fibrous web on the screen. It should be understood that the system may be modified to control the composition and thickness of the end product. For example, the distributor unit typically comprises a plurality of individual distributors, and although FIG. 1 shows schematically four distributors at 12A, 12B, 12C and 12D, this number of distributors and particular arrangement can be altered or varied depending on such factors as machine speed, capacity, type of fibers, and end product desired.

Web 22 formed on screen 14 has incorporated therein a water-insoluble superabsorbent material. In a preferred embodiment as shown in FIG. 1, a dosing unit or feed hopper 24, containing superabsorbent particles 26, is positioned in the middle of the distributor unit, i.e. between distributors 12B and 12C. In this manner, superabsorbent particles are deposited between plies of fluff laid by each distributor. That is, the superabsorbent particles are discharged from hopper 24 onto the moving layer of fluff laid down by distributors 12A and 12B, and the plies of fluff laid down by distributors 12C and 12D are laid over the superabsorbent particles. It should be understood, however, that the plies are relatively porous, and therefore the particles tend to migrate somewhat into adjacent plies. Where desired, the superabsorbent particles may be blended with the fibers in one or more distributors, such as in distributor 12B or 12C, thereby forming a web with superabsorbent particles intermixed with one or more fibrous plies of the web.

At this stage of the process, the web 22 condensed on forming wire 14 has very little integrity and requires stabilization. The web is advanced by the continuous screen, and where desired, the web first may be passed between compression rollers 28, which may be heated, to densify the web, but this step is optional. This densification step enhances the penetration of the latex into the web, and the degree or percent of densification can vary depending on such factors as the amount of hydrogel, basis weight of the web, the desired degree of penetration of the latex into the web, and the end product sought. From there, the web is transported to a suitable dispensing means 30, such as a spray nozzle, doctor blade, roller applicator, or the like, where a latex binder is applied to the surface of the loose web. A vacuum applied by suction box 31 positioned beneath the dispensing means and screen helps to draw the latex into the web. The dispensing means or applicator is essentially coextensive with the width of the web, and preferably a substantially uniform coating is applied to the web surface. However, the latex may be applied as a nonuniform, random or pattern coating, and because the latex is water-based, it will diffuse throughout the web and function as a binder when cured. The latex when cured imparts integrity to the web, and therefore some penetration of the latex is required. The extent or degree of penetration of the latex into the web is controlled by controlling the amount of latex applied and by controlling the vacuum applied to the web in that the vacuum helps to draw the latex into the web. The latex is usually applied as an aqueous emulsion, and is a thermosetting plastic. In order to activate the latex, the latex emulsion contains a suitable curing agent or cross-linking agent, and after the web is coated, the latex is cured to effect cross-linking. Most typically, curing is accomplished by passing the coated web through a hot air oven or through air drier 32, and the temperature typically ranges from about 200° to 500° F. but this depends upon the specific type of latex resin used, upon the curing agent or cross-linking agent, upon the amount of latex, the thickness of the web, the degree of vacuum, and the machine speed. It is desirable to coat both surfaces of the web with latex, and this is readily accomplished by reverse rolling the web so that the top surface at the dispensing means 30 becomes the bottom surface. Thus, web 22 is transferred to a second screen 34 and then advanced to a second dispensing means 36, including suction box 37, where latex is now applied to the opposite side. This second latex coating is likewise cured by passing the web through a second oven 38 within about the same temperature range.

The resulting web structure 40 exiting from the last oven now exhibits sufficient integrity and can be cut, rolled, packaged, etc. As shown, the web 40 is taken up on roller 42, and may be used as stock for a finished product such as of the type described below in detail.

Figure 2:
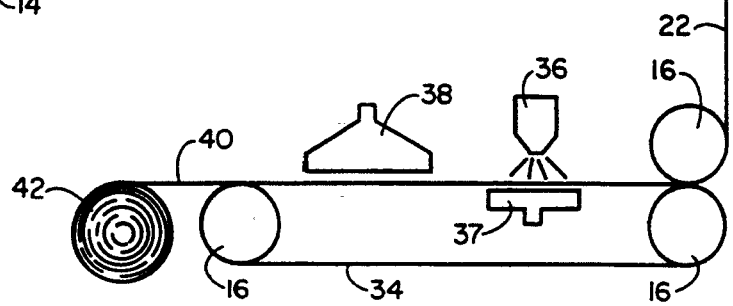
FIG. 2 is a cross-sectional view on an enlarged scale of an absorbent structure made in accordance with the present invention.

The fibrous structure made in accordance with the foregoing process is illustrated in FIG. 2. The structure, indicated generally by the numeral 44, comprises randomly distributed fibers 46, such as wood pulp fibers, and superabsorbent particles 48 are randomly distributed in the web. It will be observed that the particles of hydrogel are more concentrated in the middle zone of the web, but some particles migrate to other sections of the web. Both surfaces of the web bear a latex coating 50, which has penetrated or impregnated the web to some degree and has partially coated some of the fibers and hydrogel particles. As explained above, the penetration is controlled so as not to substantially impair the absorbent capacity of the hydrogel.

Notwithstanding the latex coating, the web is soft yet strong and absorbent, exhibiting a relatively high tensile strength and breaking length. It is desirable for fibrous structures of this type to have relatively low bulk, because a more dense web, when compared to similar structures containing no latex and of about equal absorptive capacity but of higher bulk, can be thinner yet highly absorbent and consequently less bulky. A reduction in bulk, which means a reduction in volume the web is occupying, without sacrificing significantly other desired properties is important from the standpoint of manufacturing, storage and packaging. Hence, for products of this invention the basis weight ranges from about 20 to 500 grams per square meter, and more preferably from about 75 to 350. There can be manufacturing constraints in producing a web having a basis weight lower than about 20 grams per square meter in that such a web lacks desired strength. When the basis weight exceeds the upper limit, the product may be too stiff and therefore not useful for most applications. The web structures should have a breaking length of not less than about 750 meters, and preferably not less than about 1000, as measured according to TAPPI method T 494 om-88 (except the TAPPI method was modified so that the rate of jaw separation was 100 mm/min). Breaking length, as defined by this TAPPI test is the calculated limiting length of a strip of uniform width, beyond which, if such a strip were suspended by one end, it would break of its own weight. Thus, a breaking length value less than this minimum results in a product that may be too weak for some applications.

The absorption capacity, retention, and absorption rate properties for the absorbent structures of this invention are particularly meaningful. The Gravimetric Absorbency Test is used by the industry to study and measure these properties, and the basic procedure and apparatus are described in Bergeni et al., Textile Research Journal, 37 (1967) 356, and in U.S. Pat. No. 4,357,827 to McConnell. In accordance with the test, a porous plate of glass fiber is connected to a water reservoir which is placed over an analytical balance. The porous plate is supported by a vertical slide assembly which allows one to adjust the height of the plate to the same level (or higher) as the water reservoir. Normally, the height of the porous plate is set at a hydrostatic tension of 1.5 cm over the water reservoir. This allows the sample to absorb as much fluid as it demands (demand wettability test) without flooding the sample. During the absorption and retention test, the plate height is automatically raised to 26 cm over the water reservoir. This allows the water to drain from the sample and simulate a wringing of the sample. Absorbent products used by the consumer undergo some form of pressure, and therefore the tests are conducted under 7 g/sq cm confining pressure, which about simulates a real life situation. When a sample is placed over the porous plate, the sample begins to absorb fluid. The water loss through the balance is recorded at five second intervals, and the test is terminated when the sample can no longer absorb or desorb 0.02 grams of fluid within 15 second intervals at a given height. Knowing the sample weight, the water absorption ratio can be calculated. Therefore, the absorption and retention values are based on the hypothetical value of the water absorbed by one gram of the sample. The values obtained are a measurement of the capabilities of the materials being tested, in that a higher absorption value indicates a higher absorptive capacity, and a higher retention value indicates a better wipe dry characteristic or holding the fluid under pressure.

Accordingly, the absorbent structures of this invention exhibit an absorptive capacity of not less than about six grams of a one percent saline solution per gram of structure, and preferably, about eight grams, as measured by the Gravimetric Absorbency Test. The absorption rate, which is an indication of how fast a sample can absorb fluid, can be determined from the initial slope of the absorption curve. The higher or steeper the absorption curve, the faster the absorption rate. The absorption rate depends on such factors as type of fibers, type of hydrogel, and density or basis weight of the structure. Also, the retention property is meaningful because the consumer most typically is applying some form of pressure to the structure when in use. Hence, the structures exhibit a retention capability of not less than about five grams of a one percent saline solution per gram of structure, and preferably not less than about six grams.

Any of a variety of fibers, including a blend or admixture, can be used in the absorbent structure of this invention. The fibers may be cellulosic, modified cellulosic, or synthetic, and include such fibers as wood pulp, rayon, cotton, cellulose acetate, polyester, polyethylene, polypropylene, nylon, and the like. A fibrous web comprising cellulosic fibers such as wood pulp fibers is particularly useful in such products as disposable diapers or wipes because the cellulose is liquid absorbent and therefore enhances the overall absorbency of the structure. Products of this type also advantageously use a blend of cellulosic and synthetic fibers, typically comprising about 65 to 95 weight percent cellulosic fibers, and more preferably up to about 20 percent by weight of the synthetic fiber. The synthetic fiber, which can be provided in any length including staple-length can improve the strength of the structure, but its content is frequently limited because it decreases the rate of absorbency of the structure. A structure comprising all synthetic fibers can be useful in such applications as a filter medium. Thus, the type of fiber and particular blend can be varied depending upon the end product. In addition to the foregoing uses, the structures of this invention can be used for incontinent pads, diaper core, diaper insert, and for surgical and wound bandages.

A wide variety of superabsorbent materials or hydrogels are well known and readily available from a number of sources. Superabsorbent polymers useful in the absorbent structures of this invention are substantially water insoluble but water swellable, and comprise, for example, saponified starch-polyacrylonitrile graft copolymers, starch-polyacrylic acid graft copolymers, cross-linked/grafted cellulose, saponified vinyl acetate-acrylic acid copolymers, starch grafted polyvinyl acetate, acrylic acid polymers, cross-linked polyethylene oxide, isobutylene maleic anhydride copolymers, and the like. The hydrogels used in the fibrous web structures may be the same or a mixture of absorbent polymers, and are incorporated into the web as a discontinuous solid material. The amount of hydrogel can vary widely depending on the end use of the product, and the weight percent can be determined, taking into account the end use, through experiment by one having skill in the art. For example, if the absorbent structure is used in a wipe or towel, a useful range for the hydrogel has been found to be from as low as 1 percent up to about 10 percent by weight. If used in a diaper or feminine pad, the weight percent hydrogel usually ranges from about 10 to 65 weight percent of the structure, and preferably from about 15 to 55 weight percent. If for the end use application sought, the percent hydrogel is too low, the product will not be sufficiently absorbent because the latex does obscure to some extent the absorbent properties of both the hydrogel and fibers. On the other hand, there appears to be no benefit in using an excessive amount or more than a predetermined maximum, but it should be understood that the amount can vary depending on such factors as type of fiber, the absorbent capacity of the hydrogel for the particular fluid to be absorbed, the amount of latex, and basis weight of the structure. The absorbent particulates may be in the form of fibers, flakes, particles, granules, powder, and the like. Particularly useful hydrogels comprise particles having a size of from about 40 to 700 microns. Particulate within this size range are relatively easy to handle and further ensure a rapid and even distribution of such particles in the web. Also, particulate too small have a greater tendency to migrate or sift from the structure and be lost or generate excessive dust.

The latex is applied as an aqueous emulsion or dispersion, which typically contains about 45 to 65 percent solids, and these materials are readily available from several manufacturers. Because the latex emulsions are water miscible, they may be further diluted, if desired, before being applied to the web. Also, these latex compositions are thermosetting, and in order to effect cross-linking, they contain a small amount of a suitable cross-linking agent which are well known chemical agents for this purpose, such as N-methylolacrylamide. Latices available are classified by chemical family, and those particularly useful include vinyl acetate and acrylic ester copolymers, ethylene vinyl acetate copolymers, styrene butadiene carboxylate copolymers, and polyacrylonitriles, and sold, for example, under the trade names of Airbond, Airflex and Vinac of Air Products, Inc., Hycar and Geon of Goodrich Chemical Co., and Fulatex of H. B. Fuller Company. The amount of latex used in the structure cannot be so high as to substantially impair or obscure the effective absorbent properties of the hydrogel and hydrophilic fibers, or as to impart a stiffness to the structure as to render it impractical. I have found that the latex may range from about 5 to 30 weight percent of the structure, and preferably from about 10 to 20 weight percent.

Figure 3A:
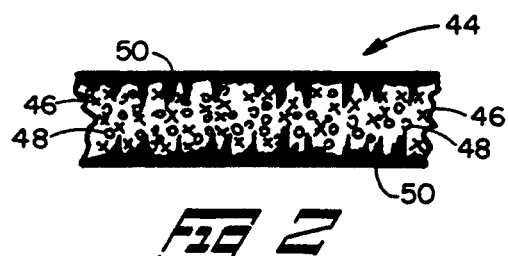
FIGS. 3A and 3B are schematic flow diagrams of a process of the invention similar to that of FIG. 1 but embodying a modification.
Figure 3B:
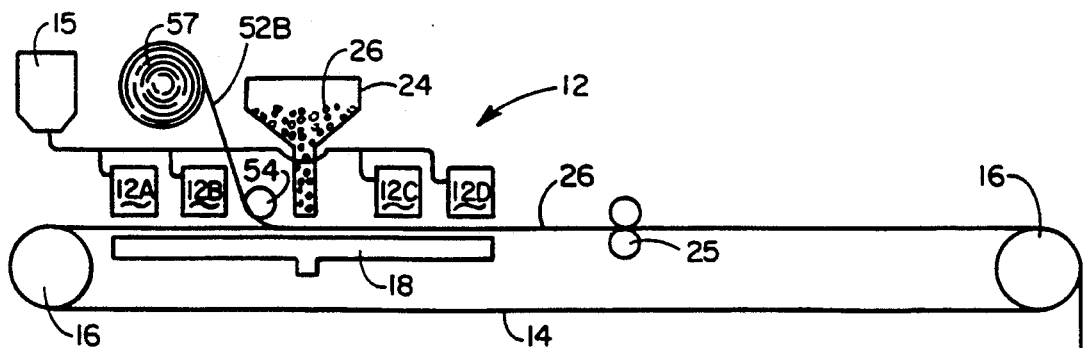

In a modified embodiment, a porous reinforcing web such as creped paper, 3D formed paper, or scrim, is incorporated into the fibrous web structure either as a surface web or as an intermediate web disposed interjacent the surfaces of the fibrous web. This embodiment is described with a particular reference to scrim. There are shown in FIGS. 3A and 3B the alternative steps in applying the scrim depending on where in the finished structure the scrim is to be positioned. The air forming system shown generally at 10 is similar to that shown in FIG. 1. If it is desired to form the reinforcing web at one outer surface of the fibrous structure as shown in FIG. 3A, the scrim 52A, which typically is a polyester or polyolefin, is fed from a source roll 53 across idler roll 54 and onto the continuous screen 14. Fibers from distributor 12A are conveyed onto the scrim to form a first ply, and the fibers become somewhat mechanically entangled with the scrim. Additional fibers and hydrogel particles are conveyed to the screen zone bearing scrim and fibers to build the desired loose web. The fibrous web is then transported to dispensing means 30 where the latex emulsion is applied, and the latex is cured on passing through hot air oven 32. The structure is then wound on roller 55.

As a further modification to this embodiment employing a scrim material, the reinforcing web may be embedded within of the fibrous web, as shown in FIG. 3B. Scrim 52B is fed from source roll 57 positioned intermediate the distributors, such as between distributors 12B and 12C as shown, and into converging relation with formed plies condensed on the screen from the distributors positioned upstream of roll 57. Superabsorbent material from hopper 24 is deposited onto the scrim surface, and additional plies of fibers are formed over the superabsorbent particles. A latex is then applied to one or both surfaces of the fibrous web, the latex is cured and the finished structure is wound on roller 58, as described above. This embodiment with the scrim interjacent the surfaces has the desirable feature in that the scrim prevents the hydrogel particles from migrating to the underside of the fibrous web thereby maintaining the particles in the desired location toward or in the vicinity of the center of the web.

Figure 4A:
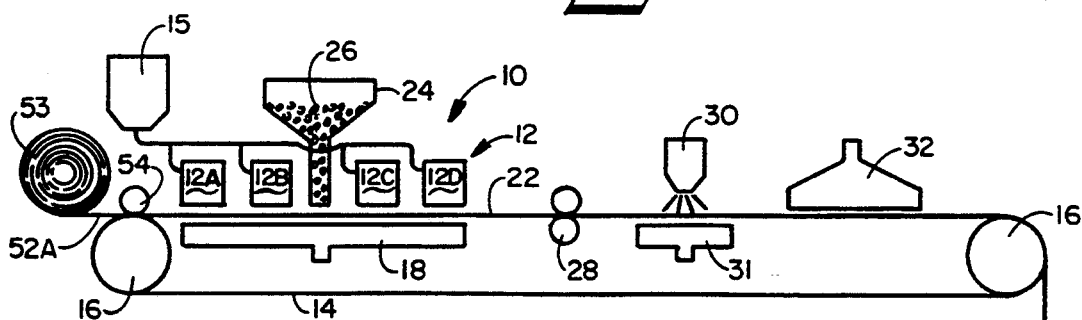
FIGS. 4A and 4B are cross-sectional views of alternative embodiments of structures made in accordance with the modified processes of FIGS. 3A and 3B.
Figure 4A:
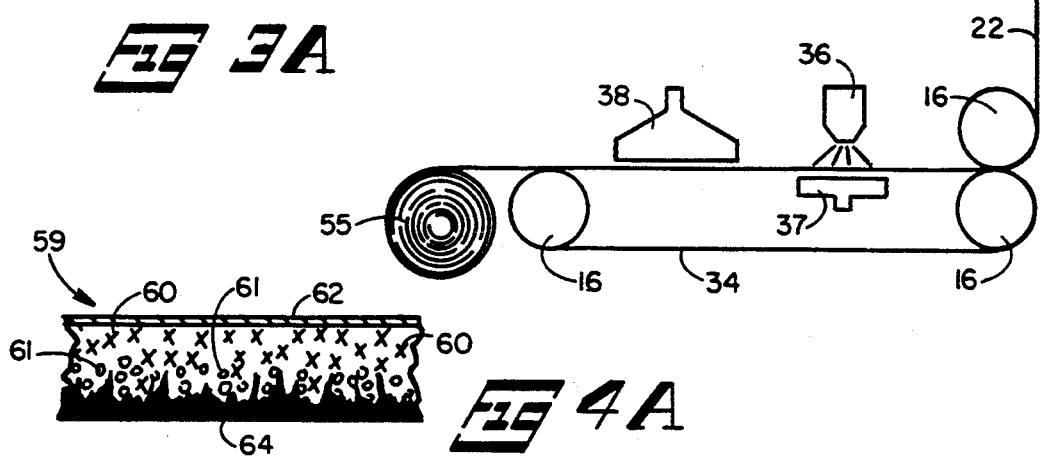
Figure 4B:
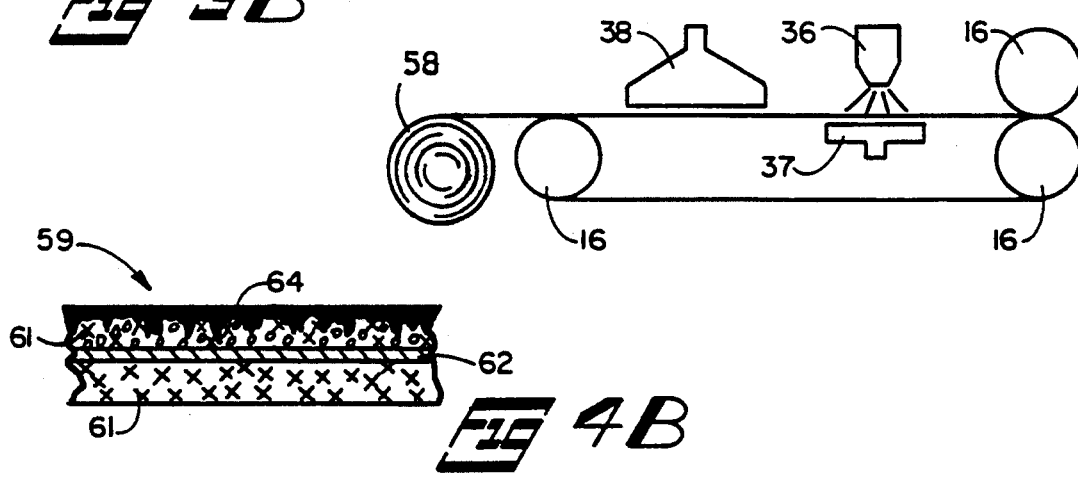

There is shown in FIGS. 4A and 4B the absorbent fibrous structure made in accordance with this embodiment utilizing a scrim. Referring to FIG. 4A, fibrous structure 59 comprises fibers 60 and hydrogel particles 61 interspersed in the web but more concentrated in the middle zone. Scrim 62 is formed on one surface of the web structure, and the opposite surface bears a cured latex coating 64. In the alternative embodiment shown in FIG. 4B, the scrim 62 is interjacent the surfaces of the fibrous web. Scrim material, which is a useful reinforcement for fibrous webs, is readily available from several sources, and typically comprises a polyester, polyethylene, polypropylene, or polyacrylic. Particularly useful materials for these embodiments of the invention include scrim having an opening ranging from about 20 to 700 microns and a denier of from about 1.2 to 5. Also, a woven scrim with openings of from about 0.1 to 7 mm can be used.

Figure 5:
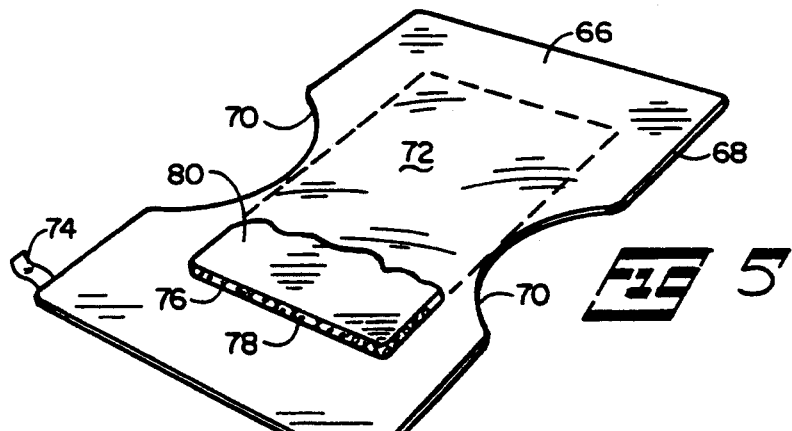
FIG. 5 is a perspective view partially broken away illustrating another embodiment of the absorbent structure of this invention and particularly useful as a diaper.

FIGS. 5 through 8, inclusive, depict useful products embodying the fibrous structure of this invention. There is shown in FIG. 5 a diaper comprising a moisture-permeable facing member 66 for the body-side of the pad, such as a nonwoven polypropylene fabric, and a puncture-impervious backing member 68, such as a polyethylene film or sheet. The diaper is the typical hour-glass configuration with cut-out leg sections 70 and crotch section 72. Tabs 74 are provided in order to secure the diaper around the waist of the wearer. In the middle portion or crotch section, there is provided the fibrous absorbent structure or core of the type shown in FIG. 2, comprising fibers 76, preferably wood pulp fibers which, if desired, may be combined with up to about 20 percent by weight synthetic fibers, and superabsorbent particles 78. A latex coating 80 is provided on both surfaces, and the latex partially penetrates the web and coats a portion only of the fibers and hydrogel particles. The diaper is sealed along the marginal edges by conventional means. The body fluid permeates fabric 66, and because of the wicking action of the fibers, the fluid is transported to all areas of the batt and absorbed by the hydrogel and fibers. The facing fabric, being liquid-permeable, is perceived by the wearer as dry even when the inner batt or web is saturated. Because the liquid absorbent structure is relatively dense and exhibits high absorbency, the diaper made utilizing this structure is exceptionally thin, and the absorbency rate compares very favorably with a more bulky pad bearing no latex. (Absorbency rate and comparative data is discussed in greater detail with reference to FIGS. 9 through 12, below.) It should be understood that the term "diaper" as used herein and in the appended claims includes adult incontinent diapers.

Figure 6:
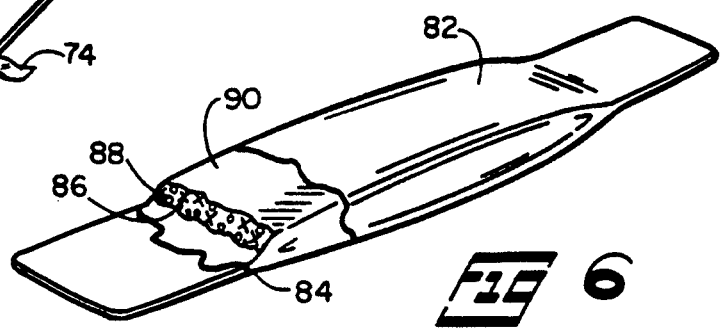
FIG. 6 is a perspective view of a sanitary napkin embodying the structure of this invention, and partially broken away to illustrate the structure.

There is shown in FIG. 6 a feminine napkin with a broken away portion to illustrate the construction of the pad. The napkin comprises a moisture-permeable facing member 82, such as a nonwoven fabric, a moisture-impermeable backing member 84, such as a polyethylene film, and the napkin is sealed along the marginal edges in a conventional manner. The absorbent core comprises fibers 86, hydrogel particles 88, and latex coating 90. The absorbent structure for this feminine pad is soft, dense, and highly absorbent.

Another useful embodiment of the invention is shown in FIG. 7, which depicts a wipe 100 comprising fibers 102, hydrogel particles 104, and latex coating 106. As with the other structures, the fibers may consist of cellulosic fibers, synthetic fibers, or a blend of fibers. The latex coating imparts integrity to the structure in that it exhibits relatively high tensile strength and breaking length without substantially impairing the absorptive capacity.

FIG. 8 shows a partial roll illustrating how a blank of the absorbent structure can be used, for example, as a diaper or diaper insert. The roll, indicated generally by the numeral 108, comprises a plurality of blanks 110, and a single blank can be separated from the roll along score line 112. Each blank is sealed along its marginal edges by a glue line or other sealant means (not shown). If the blank is to be used as a diaper, diaper insert or training pant insert, the blank can have the conventional hour-glass configuration such as shown in FIG. 5. Also, a roll of feminine napkins could be provided with the napkins rolled about its longitudinal axis (the long axis), and each napkin separable from the roll along the score line. If used as a wipe or towel, the blank can have a rectangular shape. Each blank comprises fibers 114, superabsorbent particles 116, and a latex coating 118. Because the absorbent structure has a relatively high density or low bulk, a large number of blanks can be provided in roll form, which is a convenience and advantage. For example, a roll approximately five inches in diameter on a one and one half inch core (such as for a paper towel) may comprise about 50 lineal feet. It would be impractical to form such a roll with conventional absorbent structures which are more bulky, i.e. less dense.

In the following examples, samples were made substantially in accordance with the procedure shown in FIG. 1. Accordingly, layers of fibers were airlaid and hydrogel particles deposited between layers to form the loose web. The webs were densified, both sides of each web impregnated with latex, and the webs then dried in a forced hot air oven.

EXAMPLE 1

Absorbent webs approximately 30 by 30 cm were prepared using 100% Southern pine bleached Kraft pulp from Weyerhaeuser Company at a basis weight of about 100 g/m$^2$, and 1M-1500 superabsorbent powder manufactured by Celanese Chemical Co. was added at a weight of about 80 g/m$^2$. The webs were coated on both sides with A-109 (K) latex from Air Products and Chemicals, Inc., and the resulting webs comprised about 17% by weight latex. The webs, identified as Samples "1" and "2", were tested for absorption and retention with a 1% saline solution and with water using the Gravimetric Absorbency Testing unit described above. The structures of this invention were compared with control structures prepared as above except no superabsorbent material was incorporated into the web. The results are shown in Table I below, with Sample 1 and Control "A" being tested with the saline solution and Sample 2 and Control "A" being tested with deionized water.

TABLE I

| Sample | Test Fluid | Basis Weight g/m$^2$ | Absorption g/g | Retention g/g |
|---|---|---|---|---|
| A | Saline | 120 | 9.3 | 1.3 |
| 1 | Saline | 190 | 11.3 | 8.1 |
| A | Water | 120 | 9.2 | 1.6 |
| 2 | Water | 256 | 84.5 | 58.6 |

Figure 10:
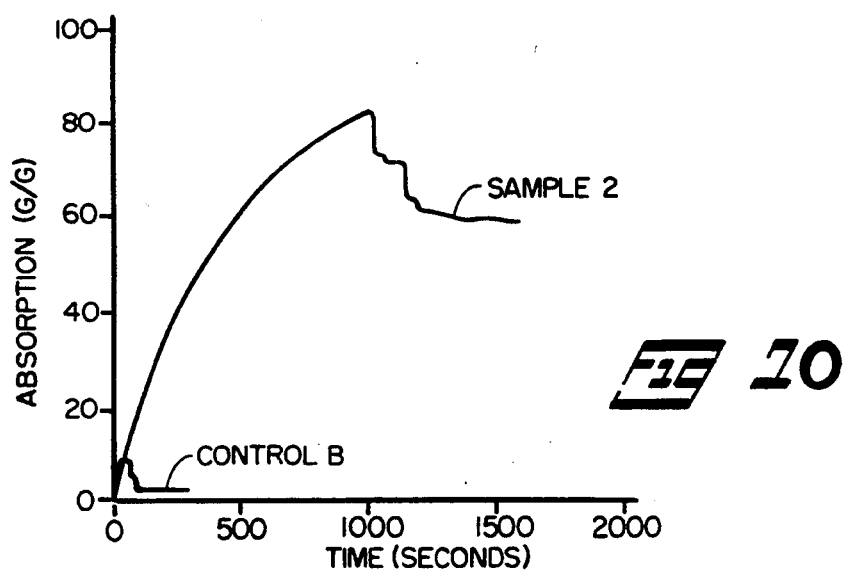

The results of the tests were plotted, and the graphs are shown in FIGS. 9 and 10. The ordinate shows absorption in g/g and the abscissa represents time in seconds. It will be observed from Table I and the graphs that the control samples achieve a relatively good maximum absorbency in about 8 or 9 seconds but when they were subjected to a higher hydrostatic tension, the capacity drops off showing poor retention. In contrast, the structures of this invention exhibit relatively good absorbency and, most significantly, exhibit exceptional retention which is important because when in actual use, the structures are subject to pressure.

EXAMPLE 2

Figure 11:
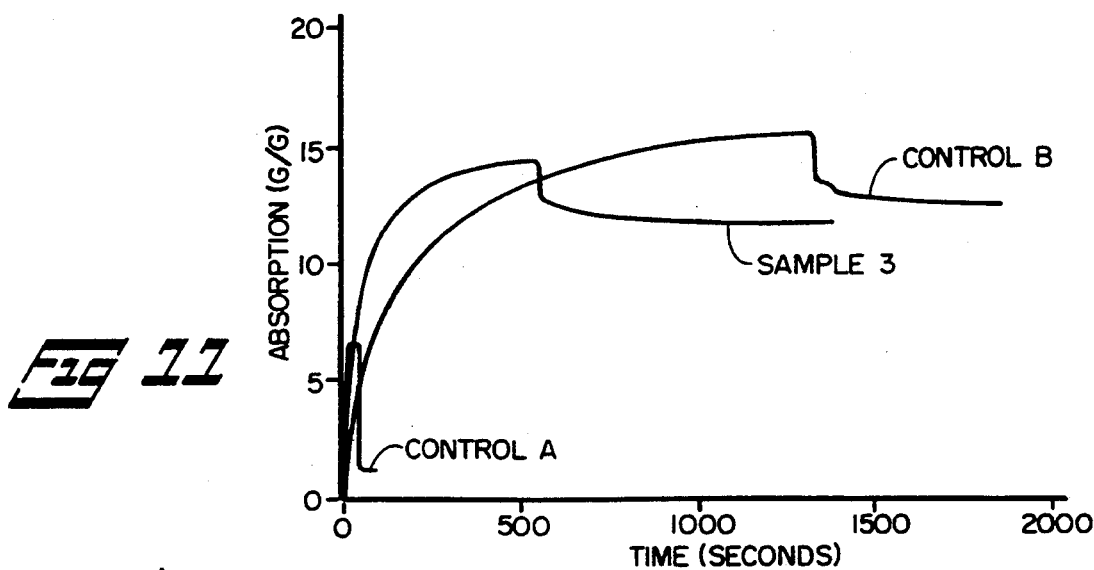
FIGS. 11 and 12 are graphs similar to FIGS. 9 and 10 showing absorption and retention curves.
Figure 12:
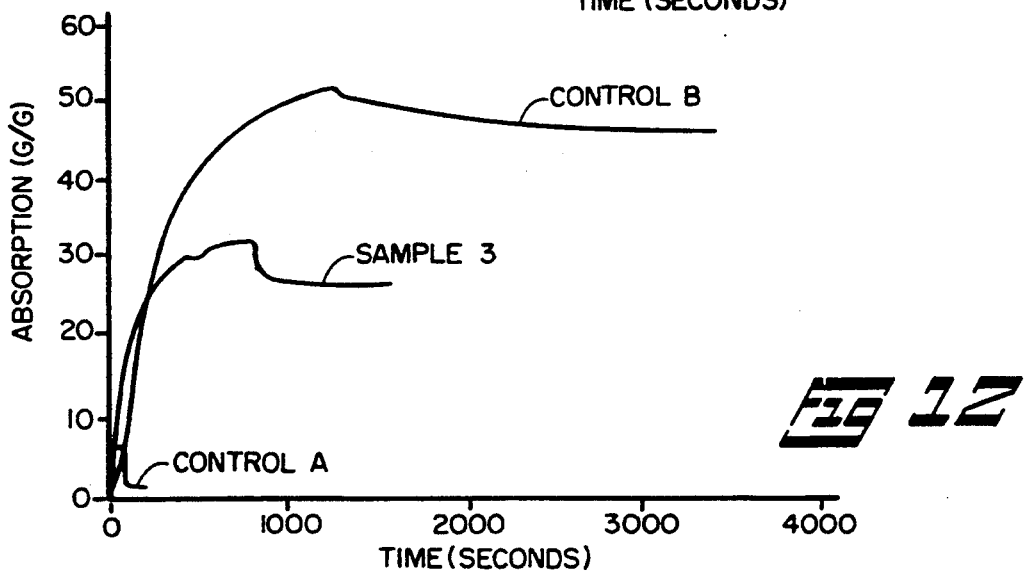

In order to further demonstrate the structure of the present invention, comparative tests were conducted as in Example 1 using the same materials for the inventive structure and for the one control (Control A). In addition, a comparison was made between a second control (Control B) comprising Kittyhawk fluff from Weyerhaeuser Company containing 20 weight percent polyethylene fiber, and hydrogel as in Example 1, but no latex was used in control B. The absorptivity results are illustrated in FIGS. 11 and 12 and Table II. It will be observed from FIG. 11 that the absorbency rate measured using a 1% saline solution for the structure of the invention is almost as fast as Control A and much faster than Control B. Thus, for the invention, maximum absorbency of about 13.76 grams per gram was achieved in about 5 minutes; whereas Control B reached the same capacity in about 9 minutes. Control B showed a maximum absorbency of about 15.6 after about 22 minutes and equaled the absorbency of the invention after about 12 minutes. However, the retention property for Control A is relatively poor, whereas the retention property for the inventive structure is very high. Similar results are shown in FIG. 12 where the absorbency rate and capacities were measured using de-ionized water. Here, the inventive product Sample "3", had a maximum absorbency of about 32.3 grams per gram in about 13 minutes and again excellent retention; whereas Control A had maximum absorbency of about 6.8 in about 1 minute and poor retention, and Control B had maximum absorbency of about 51.5 in about 21 minutes. Data shown in Table II indicates that the water absorption rate was much higher within 2 minutes for the inventive product Sample "3" as compared to the sample bonded with 20% synthetic fiber. This higher initial absorption rate is important for products such as diapers since the material should absorb fluid within 1 minute of sudden discharge.

TABLE II

| | | Absorption Rate | | | | | |
|---|---|---|---|---|---|---|---|
| | Basis Weight | Saline (1%) | | | Water | | |
| Product | g/m | ml/1 min | ml/2 min | ml/5 min | ml/1 min | ml/2 min | ml/5 min |
| Control "A" | 86 | 6.55 | — | — | 6.78 | — | — |
| Sample "3" | 170 | 9.60 | 11.63 | 13.76 | 13.71 | 18.63 | 27.74 |
| Control "B" | 311 | 5.83 | 7.54 | 11.07 | 6.37 | 13.97 | 32.67 |

Thus, as shown by the graphs in FIGS. 11 and 12, the structure of the present invention exhibits fast absorbency and excellent retention, thereby making the product a useful liquid absorptive structure such as for body fluids.

EXAMPLE 3

As a further test, the absorbent structure was made on a pilot machine using two distributors for air laying fibers and a dosing unit positioned between the distributors for depositing hydrogel particles. The web comprised JDL fluff pulp from ITT Rayonnier at a basis weight of approximately 100 g/m², Aquakeep 10 SHP superabsorbent powder at a weight of about 80 g/m² from Norsolor Chemical Company, and Vinumul 33003 latex at a weight of approximately 10 g/m²/side. The Vinumul 33003 latex is a vinyl acetate ethylene emulsion with an anionic surfactant from Vinumul which is a subsidiary of National Starch Company. The basis weight for samples tested from the web structure varied from about 177 to 227 g/m². The structure had a breaking length of about 6079 meters in the machine direction and 5111 meters in the cross direction (TAPPI T 494 om-88, described above), which shows relatively high strength for webs of this type. Absorption and retention test data in grams of solution per gram of fibrous web for a 1% saline solution are shown in Table III below.

TABLE III

| Absorption/Retention | |
| --- | --- |
| 5 seconds absorption | 3.1 g/g |
| 10 seconds absorption | 5.7 g/g |
| 15 seconds absorption | 8.2 g/g |
| maximum absorption | 12.8 g/g |
| maximum retention | 10.7 g/g |

Here again, the results show that a structure of the present invention exhibits not only relatively high absorption but excellent retention of fluid. From the foregoing, it will be observed that the structures are particularly useful in absorbent products, such as those used in absorbing body fluids and as filters.

I claim:

1. A dry laid, liquid absorbent structure comprising a dry laid fibrous web having randomly incorporated therein solid particulate of a superabsorbent material, and a latex coating on at least one surface of said fibrous web, said structure having (i) a basis weight of about 20 to 500 grams per square meter, (ii) an absorptive capacity of not less than about 6 grams of a one percent saline solution per gram of structure and (iii) a retention capability of not less than about 5 grams of a one percent saline solution per gram of structure.

2. A dry laid structure according to claim 1 wherein a porous reinforcing member is provided on at least one surface of said fibrous web.

3. A dry laid, liquid absorbent structure comprising a dry laid fibrous web, a porous reinforcing member disposed substantially interjacent the surfaces of said fibrous web, solid particulate of a superabsorbent material randomly incorporated into said fibrous web to one side of said reinforcing web, and a latex coating on at least one surface of said fibrous web, said structure having (i) a basis weight of about 20 to 500 grams per square meter, (ii) an absorptive capacity of not less than about 6 grams of a one percent saline solution per gram of structure and (iii) a retention capability of not less than about 5 grams of a one percent saline solution per gram of structure.

4. A structure according to any of claims 1, 2 or 3 wherein said structure comprises about 5 to 30 percent by weight of latex.

5. A structure according to claim 4 wherein said structure comprises about 10 to 20 percent by weight of latex.

6. A structure according to any of claims 1, 2 or 3 wherein said fibrous web comprises cellulosic fibers.

7. A structure according to any of claims 1, 2 or 3 wherein said fibrous web comprises synthetic fibers.

8. A structure according to any of claims 1, 2 or 3 wherein said fibrous web comprises an admixture of cellulosic fibers and synthetic fibers.

9. A structure according to claim 8 wherein said fibrous web comprises about 65 to 95 percent by weight wood pulp fibers.

10. A structure according to any of claims 1, 2 or 3 wherein both surfaces of said web are coated with said latex.

11. A structure according to any of claims 1, 2 or 3 wherein said superabsorbent material comprises from about 10 to 65 percent by weight of said structure.

12. A structure according to claim 11 wherein said superabsorbent material comprises from about 15 to 55 percent by weight of said structure.

13. A structure according to any one of claims 1, 2 or 3 wherein said basis weight is from about 20 to 350 grams per square meter, said absorptive capacity is not less than about 8 grams of a one percent saline solution per gram of structure, and said retention capability is not less than about 6 grams of a one percent saline solution per gram of structure.

14. A structure according to claim 3 wherein said reinforcing member is selected from group consisting of creped paper, 3-D formed paper, and scrim.

15. A disposable diaper containing an absorbent pad wherein said absorbent pad comprises a dry laid fibrous web having randomly incorporated therein about 10 to 65 weight percent of solid particulate superabsorbent material, and a latex coating on at least one surface of said fibrous web, said pad having (i) a basis weight of about 20 to 500 grams per square meter, (ii) an absorptive capacity of not less than about 6 grams of a one percent saline solution per gram of structure and (iii) a retention capability of not less than about 5 grams of a one percent saline solution per gram of structure.

16. A sanitary napkin having a liquid-permeable facing member and an opposed liquid-barrier member and an interposed dry laid, liquid absorbent structure comprising a dry laid fibrous web having randomly incorporated therein about 10 to 65 weight percent solid particulate superabsorbent material, and a latex coating on at least one surface of said fibrous web, said structure having (i) a basis weight of about 20 to 500 grams per square meter, (ii) an absorptive capacity of not less than about 6 grams of a one percent saline solution per gram of structure and (iii) a retention capability of not less than about 5 grams of a one percent saline solution per gram of structure.

17. A wipe adaptable for absorbing liquids comprising a dry laid fibrous web having randomly incorporated therein about 1 to 10 weight percent solid particulate superabsorbent material, and a latex coating on at least one surface of said fibrous web, said structure having (i) a basis weight of about 20 to 500 grams per square meter, (ii) an absorptive capacity of not less than about 6 grams of a one percent saline solution per gram of structure and (iii) a retention capability of not less than about 5 grams of a one percent saline solution per gram of structure.

18. A roll comprising a plurality of liquid absorbent pads, each of said pads separable from said roll along a transverse score line, each pad comprising a dry laid fibrous web having randomly incorporated therein solid particulate of a superabsorbent material, and a latex coating on at least one surface of said fibrous web, said structure having (i) a basis weight of about 20 to 500 grams per square meter, (ii) an absorptive capacity of not less than about 6 grams of a one percent saline solution per gram of structure and (iii) a retention capability of not less than about 5 grams of a one percent saline solution per gram of structure.

* * * * *